(12) United States Patent
Ralph et al.

(10) Patent No.: US 6,644,087 B1
(45) Date of Patent: Nov. 11, 2003

(54) ROD BENDER FOR BENDING SURGICAL RODS

(75) Inventors: James D. Ralph, Seaside Park, NJ (US); Stephen Tatar, Montville, NJ (US); Thomas N. Troxell, Pottstown, PA (US)

(73) Assignee: Third Millennium Engineering, LLC, Summit, NJ (US)

( * ) Notice: Subject to any disclaimer, the term of this patent is extended or adjusted under 35 U.S.C. 154(b) by 0 days.

(21) Appl. No.: 10/205,873

(22) Filed: Jul. 26, 2002

(51) Int. Cl.[7] .............................. B21K 1/74; B21D 9/08
(52) U.S. Cl. ..................... 72/213; 72/389.1; 72/390.4
(58) Field of Search ..................... 72/211, 212, 213, 72/217, 389.1, 389.4, 389.5, 390.4

(56) References Cited

U.S. PATENT DOCUMENTS

| | | | | |
|---|---|---|---|---|
| 1,054,132 A | * | 2/1913 | Miner ........................ | 72/213 |
| 2,277,204 A | * | 3/1942 | Byler ........................ | 72/213 |
| 2,339,855 A | * | 1/1944 | Hodil et al. ................. | 72/213 |
| 2,779,382 A | * | 1/1957 | Anello ....................... | 72/390.4 |
| 3,018,818 A | * | 1/1962 | Swanson ..................... | 72/213 |
| 3,271,990 A | * | 9/1966 | Mitchell .................... | 72/390.6 |
| 3,918,286 A | * | 11/1975 | Whitehead ................... | 72/213 |
| 4,005,593 A | * | 2/1977 | Goldberg .................... | 72/213 |
| 4,446,711 A | * | 5/1984 | Valente ...................... | 72/213 |
| 4,936,131 A | * | 6/1990 | Gray ......................... | 72/213 |
| 5,237,847 A | * | 8/1993 | Owens ....................... | 72/213 |
| 5,461,897 A | * | 10/1995 | Gray et al. .................. | 72/213 |
| 5,490,409 A | | 2/1996 | Weber | |
| 5,528,921 A | * | 6/1996 | Herman ...................... | 72/389.1 |
| 5,548,985 A | | 8/1996 | Yapp | |
| 5,615,572 A | * | 4/1997 | Johnson et al. ............... | 72/389.1 |
| 6,035,691 A | | 3/2000 | Lin et al. | |

* cited by examiner

*Primary Examiner*—David B. Jones
(74) *Attorney, Agent, or Firm*—Joseph P. Errica, Esq.; Timothy J. Bortree, Esq.

(57) ABSTRACT

A rod bender includes a ram shaft, having a distal end with an arcuate rod contact surface, that is movable along a shaft path that passes between two rollers, each having a curved roller surface. Each of the rollers is positionable, in an analog manner, at a variety of positions along a respective roller path, relative to a distal position of the arcuate rod contact surface. A straight rod, positioned against the rollers so that it spans the space separating the rollers and crosses the shaft path, can be rammed with the ram shaft so that the rod is bent into an arc. The rod is bent as the movement of the ram shaft pushes the arcuate rod contact surface forward against the center of the rod, while the curved roller surfaces prevent corresponding forward movement of the lateral portions of the rod.

14 Claims, 7 Drawing Sheets

ROD BENDER FOR BENDING SURGICAL RODS

FIELD OF THE INVENTION

This invention relates generally to devices for bending surgical rods and more specifically to rod benders capable of bending a surgical rod into multiple different arc shapes.

BACKGROUND OF THE INVENTION

Surgeons frequently use metal rods to facilitate the fusing of adjacent vertebrae in the spine to remedy a variety of spinal disorders. The spine, however, is curved, and the rods must often be bent to conform to the curvature of the bone in order to maximize affixation between the secured vertebrae. In some cases, pre-bent rods are employed by surgeons. However, commercially available pre-bent rods are provided only in specific sizes. While the general desired configuration of a rod for particular portions of the skeleton can be determined by x-ray and imaging techniques, in many instances it is desirable to confirm the desired configuration of the rod by visual inspection of the vertebrae at issue. Accordingly, it is desirable that the surgeon be able to shape bendable metallic rods during surgery to meet the specific anatomical fit requirements of a patient. Attempts have been made to bend rods into the desired configuration in the operating room during surgery. However, bending in many cases was effected employing pliers, vices, and hammers.

More sophisticated rod benders have been developed and are, in general, known, but many of such devices typically can bend the rod only to a single particular radius. One prior art device that can be used to bend the rod into one of three radii is disclosed in U.S. Pat. No. 5,490,409, entitled "Adjustable Cam Action Rod Bender for Surgical Rods". The handheld rod bender disclosed therein includes an adjustable cam with three positions for providing three different radii into which a rod can be bent. While this provides an advantage in that more than one arc radius is provided by the device, surgeons will frequently encounter the need to bend the rod into an arc having a radius that is different than that provided by this device.

Another prior art device, which can bend the rod into one of several desired curved shapes, is disclosed in U.S. Pat. No. 6,035,691, entitled "Adjustable Rod Bending Device for a Corrective Spinal Rod which is Used in a Surgical Operation." The table-top rod bender disclosed therein has a plurality of adjustable rollers that when brought to bear against a straight rod, cause the rod to be bent into the curved shape defined by the relative positions of the roller ends. While providing a plurality of potential arc shapes, this device is time-consuming, inasmuch as each adjusting bolt must be positioned correctly before the rod is bent.

Therefore, there is a need for a rod bender that enables the rod to be bent into several differently dimensioned arcs.

There is also a need for a rod bender that enables analog adjustment of the dimensions of the arc into which the rod will be bent.

There is also a need for a rod bender that can be used to quickly set the dimensions of the arc into which the rod will be bent.

Other needs met by the invention not explicitly stated will be set forth and will be more clearly understood in conjunction with the descriptions of the preferred embodiments disclosed hereafter.

SUMMARY OF THE INVENTION

A rod bender of the invention includes a ram shaft that is movable along a shaft path that passes between two rollers. The distal end of the ram shaft has an arcuate rod contact surface, and the rollers each have a curved roller surface. Each of the rollers is positionable, in an analog manner, at a variety of positions along a respective roller path, relative to a distal position of the arcuate rod contact surface (the position of the arcuate rod contact surface when the ram shaft is in a distal rod engaging position). A straight rod positioned against the rollers so that it spans the space separating the rollers and crosses the shaft path, can be rammed with the ram shaft so that the rod is bent into an arc. More particularly, the rod is bent as the movement of the ram shaft pushes the arcuate rod contact surface forward against the center of the rod, while the curved roller surfaces prevent corresponding forward movement of the lateral portions of the rod.

The movement of the ram shaft along the shaft path is effected by operation of a lever mechanically connected to the ram shaft by a cam. Movement of the lever correspondingly moves the ram shaft between a proximal rod disengaging position (where the distal end of the ram shaft is backward of the rollers) and a distal rod engaging position (wherein the distal end of the ram shaft is forward of the rollers). When the ram shaft is moved from the rod disengaging position to the rod engaging position, the straight rod spanning the space between the rollers is bent as the distal end of the ram shaft moves forward of the rollers.

At least one dimension of the arc into which the rod is bent is determined by the position of the rollers relative to the distal position of the arcuate rod contact surface. The position of each roller along its respective roller path is adjustable in an analog manner to any of a plurality of positions on the roller path.

More particularly in a first preferred embodiment, each of the rollers is rotatably mounted to a distal end of a respective roller shaft, and each roller shaft has a proximal end that is rotatably mounted about a roller shaft hinge point forward of the ram shaft. For example, to bend the rod into a tighter arc shape, the rollers are brought farther forward along the roller paths (by swinging the roller shafts about the shaft hinge point, so that the angle between the curved roller surfaces and the arcuate rod contact surface is smaller) prior to setting the rod and moving the ram shaft forward. Or, for example, to bend the rod into a looser arc shape, the rollers are positioned farther backward along the roller paths (by swinging the roller shafts about the shaft hinge point, so that the angle between the curved roller surfaces and the arcuate rod contact surface is larger) prior to setting the rod and moving the ram shaft forward.

Further in the first preferred embodiment, the setting of each roller along its roller path is effected by rotation of a respective knob at the end of a respective roller adjustment shaft. Each roller adjustment shaft cooperates with a coupling pin to swing its associated roller shaft about the hinge point. More particularly, each roller adjustment shaft has a threaded portion, and each coupling pin has a bore that is correspondingly threaded, so that rotation of the roller adjustment shaft moves the coupling pin along the threaded portion. For example, clockwise rotation of the roller adjustment shaft moves the coupling pin forward along the threaded portion (i.e., away from the knob), and counter-clockwise rotation of the roller adjustment shaft moves the coupling pin backward along the threaded portion (i.e., toward the knob). The cooperating threads prevent movement of the coupling pin unless the roller adjustment shaft is rotated (this secures the coupling pin at the desired location once the knob is released). Further, each roller shaft has a slot or bore within which the coupling pin fits to engage the roller shaft, so that when the coupling pin is moved along the threaded portion, the coupling pin pushes against the side of the bore to push the roller shaft to swing the roller shaft about the hinge point.

Alternatively, in a second preferred embodiment, each of the rollers is rotatably mounted to a support block that extends parallel to the plane and perpendicular to the shaft path. Movement of the support block, which movement is parallel to the shaft path, moves both of the rollers relative to the distal position of the arcuate rod contact surface. In this embodiment, the movement of each roller along its roller path (and the securing of each roller at a desired position along the roller path) is effected by rotation of a knob at the end of a roller adjustment shaft. The roller adjustment shaft has a threaded portion, and the support block has a bore that is correspondingly threaded, so that rotation of the roller adjustment shaft (about a longitudinal axis of the roller adjustment shaft) moves the support block along the threaded portion. The cooperating threads prevent movement of the support block unless the roller adjustment shaft is rotated (this secures the support block at the desired location once the knob is released).

DETAILED DESCRIPTION OF THE PREFERRED EMBODIMENTS

Figure 1:
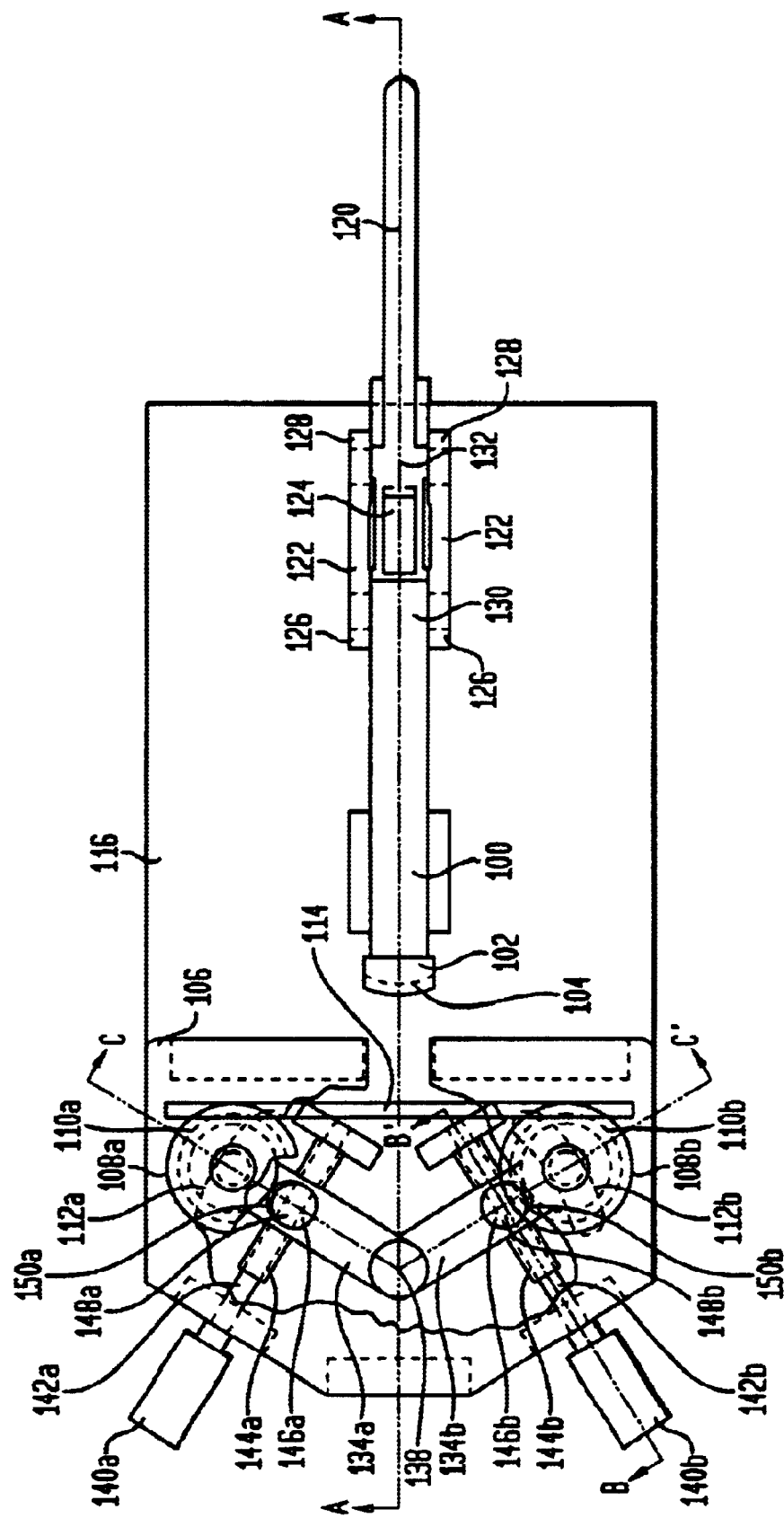
FIG. 1 is a top view of a rod bender assembly of a first preferred embodiment of the invention, showing a lever and ram shaft in a backward rod disengaging position.
Figure 2:
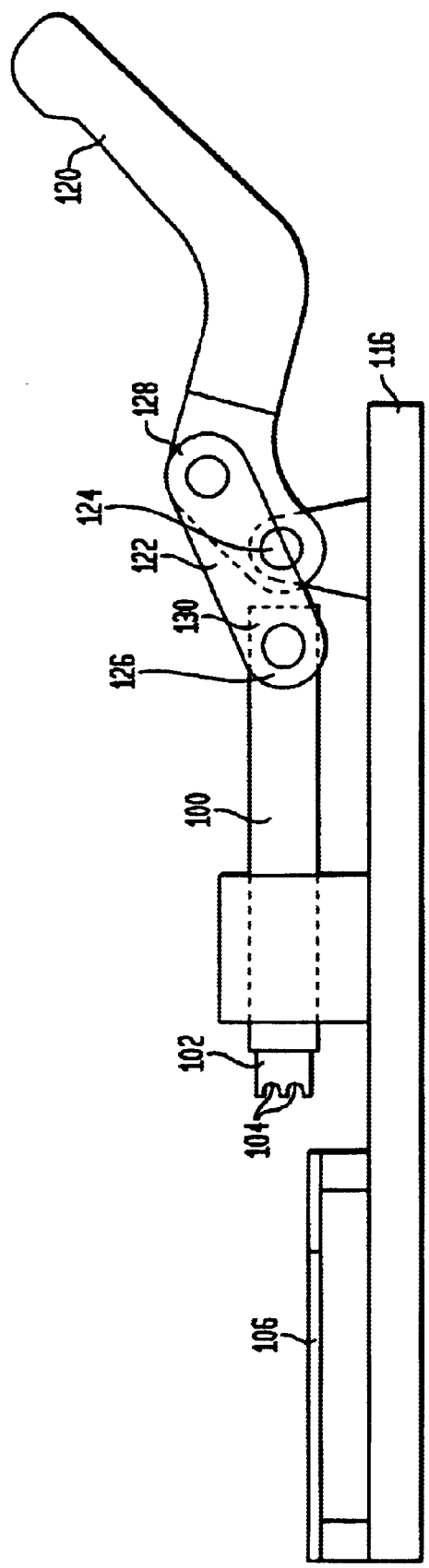
FIG. 2 is a side cutaway partial view of the rod bender assembly of FIG. 1, with the cutaway taken along line A—A' of FIG. 1.
Figure 3:
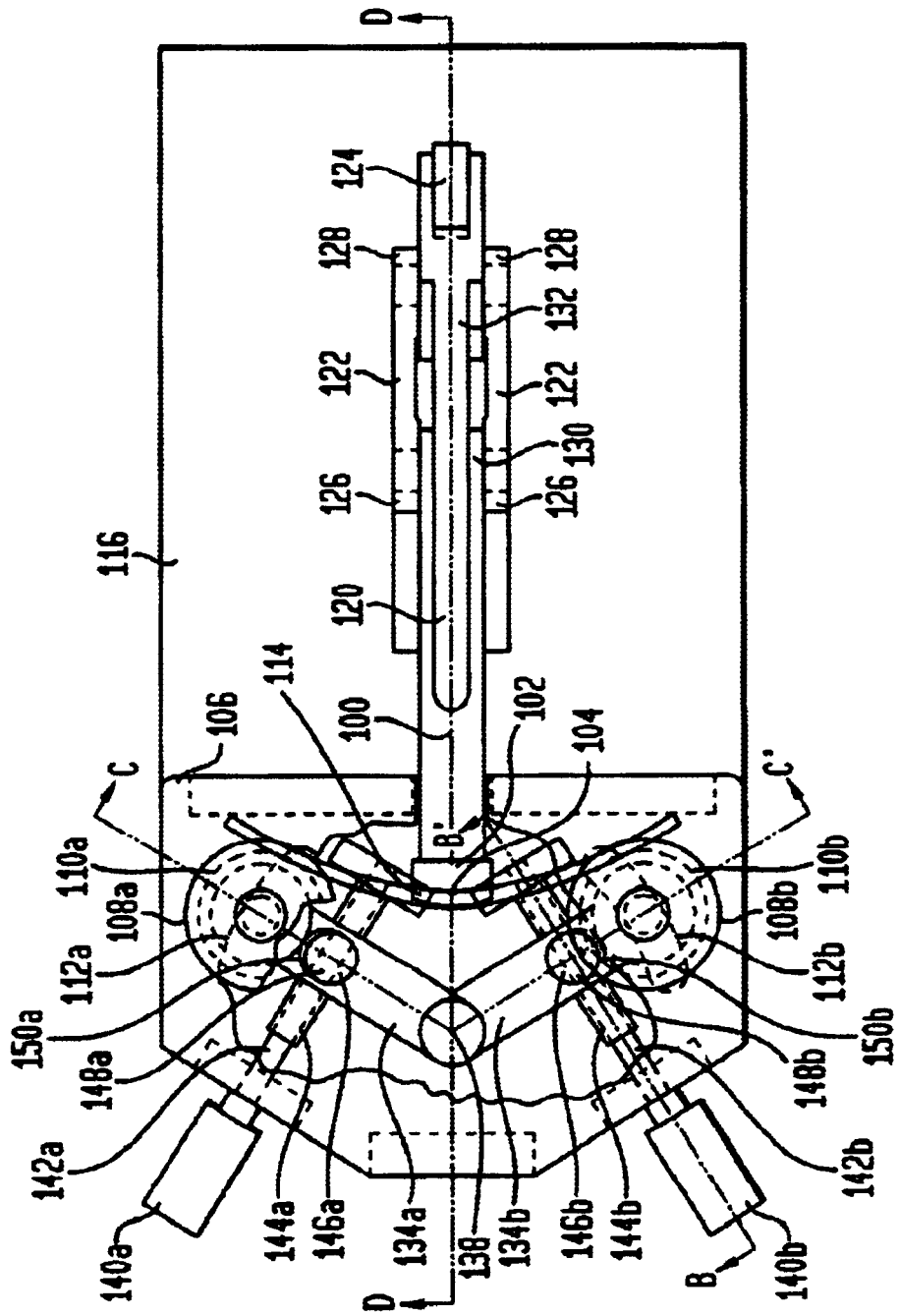
FIG. 3 is a top view of the rod bender assembly of FIG. 1, showing a lever and ram shaft in a forward rod engaging position.
Figure 4:
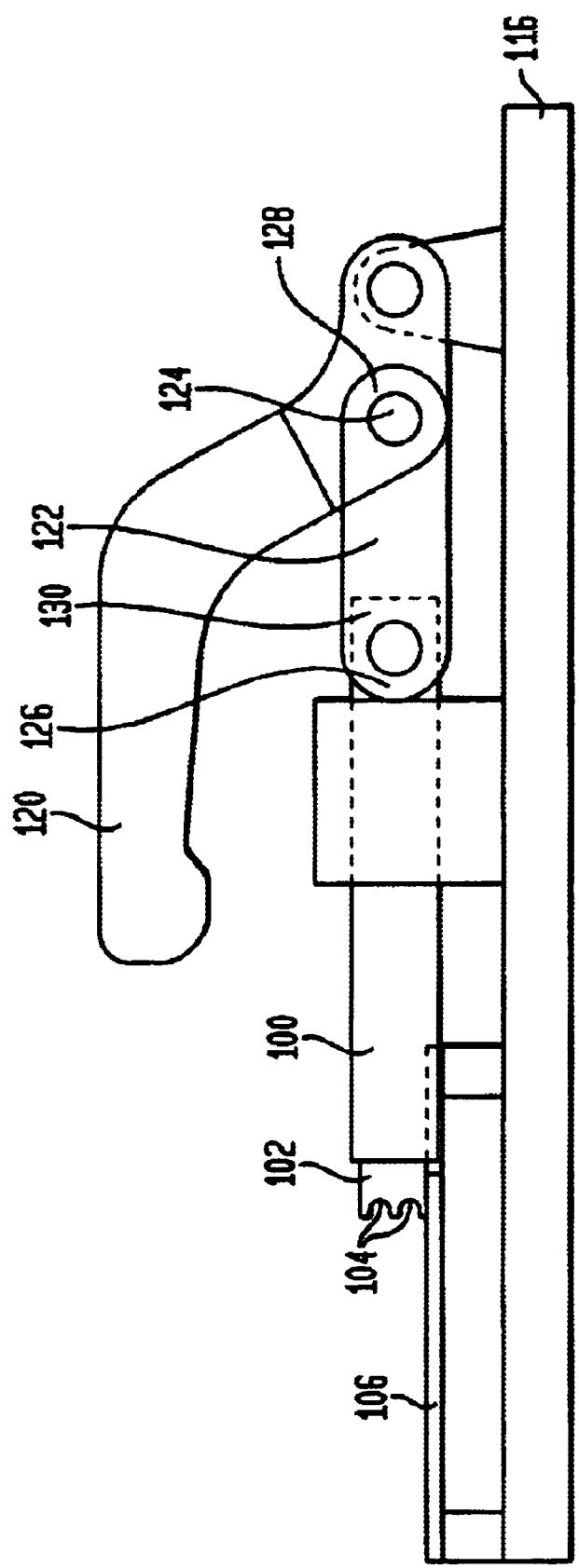
FIG. 4 is a side cutaway partial view of the rod bender assembly of FIG. 1, with the cutaway taken along line D—D' of FIG. 3.
Figure 5:
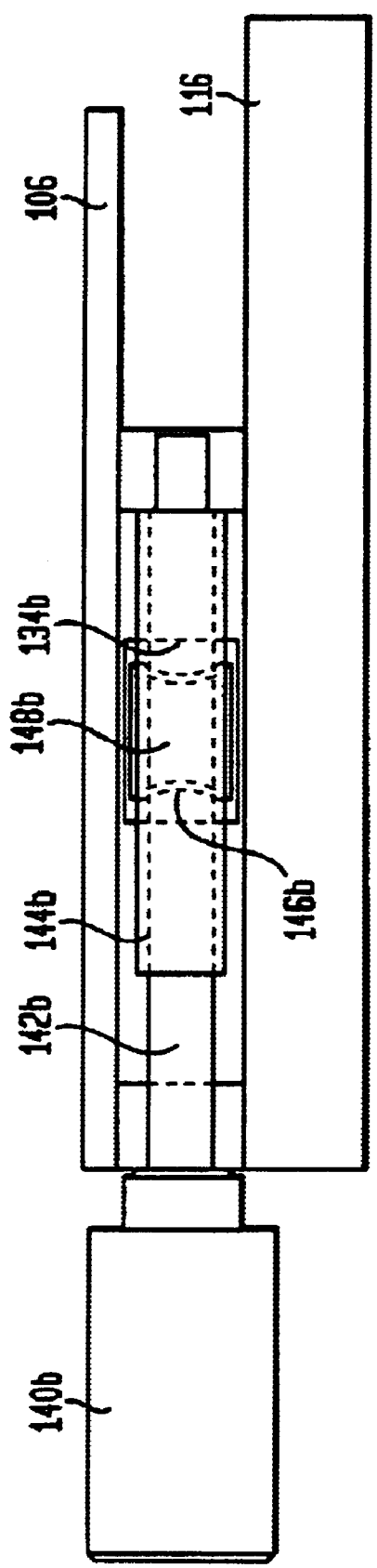
FIG. 5 is a cutaway partial view of the rod bender assembly of FIG. 1, with the cutaway taken along line B–B' of FIGS. 1 and 3.
Figure 6:
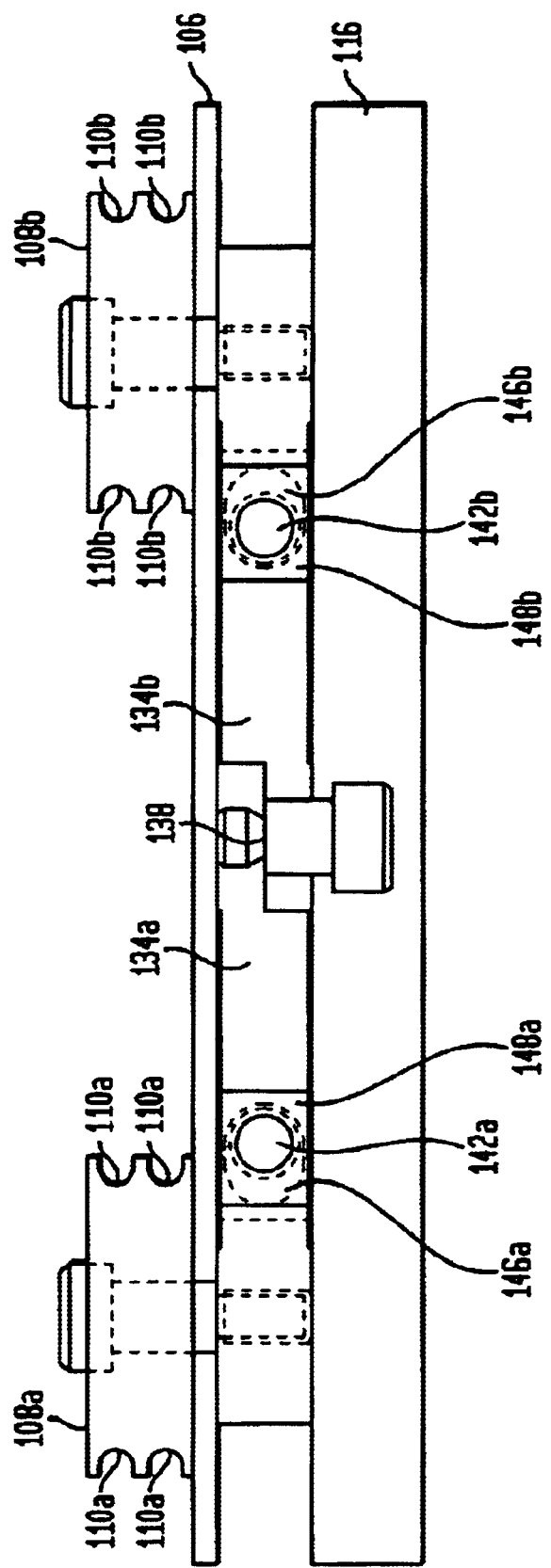
FIG. 6 is a cutaway partial view of the rod bender assembly of FIG. 1, with the cutaway taken along line C—C' of FIGS. 1 and 3.

While the invention will be described more fully hereinafter with reference to the accompanying drawings, in which particular embodiments and methods are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the invention and not as limiting of such broad scope. Like numbers refer to similar features of like elements throughout.

Referring now to FIGS. 1–6, which show top views (FIGS. 1 and 3) and side cutaway views (FIGS. 2, 4 and 5–6) of a rod bender of a first preferred embodiment of the invention, the rod bender includes a ramming surface providing element (e.g., a ram shaft 100), having a distal end 102 with a ramming surface (e.g., an arcuate rod contact surface 104), that is movable along a ramming path (e.g., a shaft path) that passes between two resistance surface providing elements (e.g., rollers 108a,108b), each having a resistance surface (e.g., a curved roller surface 110a,110b). The ram shaft 100 is moveable along the shaft path between a proximal rod disengaging position (see FIGS. 1 and 2) and a distal rod engaging position (see FIGS. 3 and 4), which correspondingly move the arcuate rod contact surface 104 into a proximal contact surface position and a distal contact surface position, respectively. Each of the rollers 108a,108b is positionable, in an analog manner, at a variety of positions along a respective roller path (defined in this embodiment by curved slots 112a,112b in a platform 106 held off the base 116 of the rod bender assembly, the base 116 establishing a plane to which the ram shaft 100 extends in parallel and moves in parallel; it should be understood that the slots or paths can be linear, rather than curved, in other embodiments), relative to the distal contact surface position of the arcuate rod contact surface 104. A straight rod 114 positioned against the rollers 108a,108b so that it spans the space separating the rollers 108a,108b and crosses the shaft path (for this positioning, see FIGS. 1 and 2), can be rammed with the ram shaft 100 so that the rod 114 is bent into an arc (for this result, see FIGS. 3 and 4). More particularly, the rod 114 is bent as the movement of the ram shaft 100 pushes the arcuate rod contact surface 104 forward against the center of the rod 114, while the curved roller surfaces 110a,110b prevent corresponding forward movement of the lateral portions of the rod 114. (Preferably, as shown, the arcuate rod contact surface 104 and each of the curved roller surfaces 110a,110b respectively has a plurality of parallel troughs formed thereon within one of which the rod 114 seats when the rod 114 is in contact therewith. This allows a plurality of rods, one in each trough, to be bent simultaneously to have the same arc dimensions.)

The movement of the ram shaft 100 along the shaft path is effected by operation of a leverage providing element (e.g., a lever 120) mechanically connected to the ram shaft 100 by a cam element (e.g., a cam 122). The lever 120 hinges about a lever hinge point 124 so that it can be rotated, about a lever hinge axis parallel to the plane and perpendicular to the ramming path, between a backward proximal position (see FIGS. 1 and 2) and a forward distal position (see FIGS. 3 and 4). Ends 126,128 of the cam 122 are hinged to the proximal end 130 of the ram shaft 100 and a central portion 132 of the lever 120, respectively, so that rotation of the lever 120 about the lever hinge axis correspondingly moves the ram shaft 100 between the proximal rod disengaging position (see FIGS. 1 and 2) and the distal rod engaging position (see FIGS. 3 and 4). When the ram shaft 100 is in the proximal rod disengaging position, the straight rod 114 (see FIGS. 1 and 2) can be positioned against the rollers 108a,108b, because the distal end 102 of the ram shaft 100 is backward of the rollers 108a,108b. When the ram shaft 100 is subsequently moved to the distal rod engaging position (see FIGS. 3 and 4), the rod 114 is bent as the distal end 102 of the ram shaft 100 moves forward of the rollers 108a,108b and correspondingly the arcuate rod contact surface 104 is moved toward the distal contact surface position. The use of the lever 120 provides leverage for the surgeon to apply sufficient force to the ram shaft 100 to bend the rod 114.

At least one dimension of the arc into which the rod 114 is bent is determined by the position of the rollers 108a,108b relative to the distal contact surface position of the arcuate rod contact surface 104. More particularly, the rod 114 is bendable into any one of a plurality of arc shapes, and wherein each possible positioning of the rollers 108a,108b determines a respective one of the plurality of arc shapes. The position of each roller 108a,108b along its respective roller path 112a,112b is adjustable in an analog manner to any of a plurality of positions on the roller path 112a,112b, including a proximal roller position and a distal roller position. More particularly, each of the rollers 108a,108b is rotatably mounted (with a rotation axis perpendicular to the plane) to a distal end of a respective support shaft (e.g., a roller shaft 134a,134b) (each roller 108a,108b is rotatably mounted to reduce friction between the curved roller surface 110a,110b and the rod 114 during the bending of the rod 114) that extends parallel to the plane, and each proximal end of the roller shaft 134a,134b rotates (with a rotation axis perpendicular to the plane) about a roller shaft hinge point 138 forward of the ram shaft 100 as shown. For example, to bend the rod 114 into a tighter arc shape, the rollers 108a,108b are brought toward their proximal positions (so that the angle between the curved roller surfaces and the arcuate rod contact surface is smaller) prior to setting the rod 114 and moving the ram shaft 100 forward. Or, for example, to bend the rod 114 into a looser arc shape, the rollers 108a,108b are brought toward their distal positions (so that the angle between the curved roller surfaces and the arcuate rod contact surface is larger) prior to setting the rod 114 and moving the ram shaft 100 forward. In this embodiment, the movement of each roller 108a,108b along the roller path 112a,112b is independent of the movement of the other roller 108a,108b along the roller path 112a,112b, although the invention encompasses embodiments where the movement of each roller 108a,108b along the roller path 112a,112b is dependent upon the movement of the other roller 108a,108b along the roller path 112a,112b (e.g., as in the second preferred embodiment described below) and/or embodiments where the placement of one of the rollers 108a,108b at a position causes the other roller 108a,108b to be placed in a corresponding opposing position. This can be accomplished mechanically or otherwise.

In this embodiment, the movement of each roller 108a,108b along its roller path 112a,112b (and the securing of each roller 108a,108b at a desired position-along the roller path 112a,112b) is effected by rotation of a respective knob 140a,140b at the end of a respective roller adjustment shaft 142a,142b. Each roller adjustment shaft 142a,142b cooperates with a coupling element (e.g., a coupling pin 148a, 148b) to swing its associated roller shaft 134a,134b about the hinge point 138. More particularly, each roller adjustment shaft 142a,142b has a threaded portion 144a,144b, and each coupling pin 148a,148b has a bore 146a,146b that is correspondingly threaded, so that rotation of the roller adjustment shaft 142a,142b (about a longitudinal axis of the roller adjustment shaft) moves the coupling pin 148a,148b along the threaded portion 144a,144b (the coupling pin 148a,148b is prevented from rotating by virtue of being held in the slot 150a,150b, discussed below, and being held between the platform 106 and the base 116, as best seen in FIGS. 2 and 4–6). For example, clockwise rotation of the roller adjustment shaft 142a,142b (about its longitudinal axis) moves the coupling pin 148a,148b forward along the threaded portion 144a,144b (i.e., away from the knob 140a, 140b), and counterclockwise rotation of the roller adjustment shaft 142a,142b (about its longitudinal axis) moves the coupling pin 148a,148b backward along the threaded portion 144a,144b (i.e., toward the knob 140a,140b). The cooperating threads prevent movement of the coupling pin 148a,148b unless the roller adjustment shaft 142a,142b is rotated (this secures the coupling pin 148a,148b at the desired location once the knob 140a,140b is released). Further, each roller shaft 134a,134b has a slot (e.g., a bore 150a,150b) within which the coupling pin 148a,148b fits to engage the roller shaft 134a,134b, so that when the coupling pin 148a,148b is moved forward along the threaded portion 144a,144b, the coupling pin 148a,148b pushes against the side of the bore 150a,150b to push the roller shaft 134a,134b to swing the roller shaft 134a,134b about the hinge point 138 to bring the roller 108a,108b forward along the roller path 112a,112b, and so that when the coupling pin 148a,148b is moved backward along the threaded portion 144a,144b, the coupling pin 148a,148b pushes against the side of the bore 150a,150b to push the roller shaft 134a,134b to swing the roller shaft 134a,134b about the hinge point 138 to bring the roller 108a,108b backward along the roller path 112a,112b. Due to a preferably tight tolerance fit of the coupling pin 148a,148b between the sides of the bore 150a,150b against which the coupling pin 148a,148b pushes, the securing of the coupling pin 148a,148b at the desired location (once the knob 140a,140b is released as discussed above), secures the roller shaft 134a,134b and the roller 108a,108b at the desired location once the knob 140a,140b is released. It should be noted, as shown, that the bore 150a,150b has a more oblong cross-sectional area than the coupling pin 148a,148b so that the movement of the coupling pin 148a, 148b in a straight line (along the threaded portion 144a, 144b) is accommodated as the roller shaft 134a,134b moves in an arc (rotating about the hinge point 138). It should be further noted, as shown, that preferably, the arcuate rod contact surface 104 of the ram shaft 100 defines an arc at least as tight as the tightest arc into which the rod 114 can be bent given the limitations of the roller paths 112a,112b and the extent of the shaft path.

Figure 7:
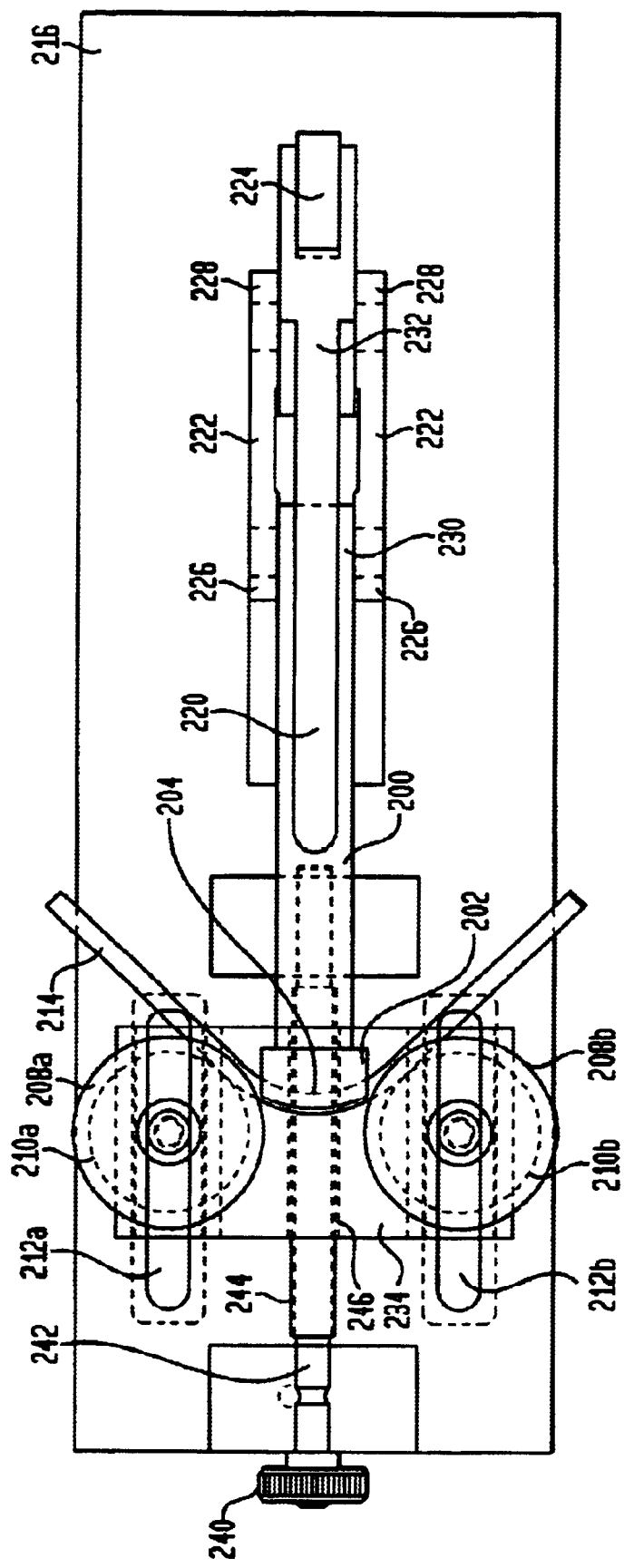
FIG. 7 is a top view of a rod bender assembly of a second preferred embodiment of the invention, showing a lever and ram shaft in a forward rod engaging position.

Referring now to FIG. 7, which shows a top view of a rod bender of a second preferred embodiment of the invention, similar to the rod bender of the first preferred embodiment with some exceptions that will be identified below. Accordingly, items that are similar in structure and function to corresponding items in the first preferred embodiment are similarly referenced here for the second preferred embodiment, but with reference numerals in the 200s rather than the 100s. For example, the moveable ram shaft 200 similarly has an arcuate rod contact surface 204 at a distal end 202, and is similarly operated by a lever 220 connected to a proximal end 230 of the ram shaft 200 with a cam 22 to move the arcuate rod contact surface 204 between a proximal contact surface position (not shown, but similar to that in FIGS. 1 and 2) and a distal contact surface position (see FIG. 7). As with the first preferred embodiment, the ram shaft path passes between the two rollers 208a,208b, each having a curved roller surface 210a,210b that is rotatably mounted about a rotation axis that is perpendicular to the plane of the base 216. Therefore, a straight rod 214 positioned so that it spans the space separating the rollers 208a,208b and crosses the shaft path (similar to the positioning in FIGS. 1 and 2 for the first preferred embodiment), can be rammed with the ram shaft 200 so that the rod 214 is bent into an arc (see FIG. 7). More particularly, the rod 214 is bent as the movement of the ram shaft 200 pushes the arcuate rod contact surface 204 forward against the center of the rod 214, while the curved roller surfaces 210a,210b prevent corresponding forward movement of the lateral portions of the rod 214. (Preferably, as in the first preferred embodiment, the arcuate rod contact surface 204 and each of the curved roller surfaces 210a,210b respectively has a plurality of parallel troughs formed thereon within one of which the rod 214 seats when the rod 214 is in contact therewith. This allows a plurality of rods, one in each trough, to be bent simultaneously to have the same arc dimensions.)

Again, at least one dimension of the arc into which the rod 214 is bent is determined by the position of the rollers 208a,208b relative to the distal contact surface position of the arcuate rod contact surface 204. In this embodiment, however, each roller 208a,208b is moveable along a respective roller path (defined in this embodiment by linear tracks 212a,212b in the base 216; it should be understood that the tracks or paths can be curved, rather than linear, in other embodiments) that is parallel to the shaft path. Further, in this embodiment, both of the rollers 208a,208b are rotatably mounted (with a rotation axis perpendicular to the plane) at respective ends of a support member (e.g., a support block 234) that extends beneath the rollers 208a,208b parallel to the plane and perpendicular to the shaft path. Movement of the support block 234, which movement in this embodiment is parallel to the shaft path, moves both of the rollers 208a,208b, forward along the roller paths 212a,212b (to establish a tighter arc shape) or backward along the roller paths 212a,212b (to establish a looser arc shape), relative to the distal contact surface position of the arcuate rod contact surface 204. In this embodiment, the movement of each roller 208a,208b is dependent on the movement of the other roller 208a,208b, although the invention encompasses embodiments where the movement of each roller 208a,208b is independent of the movement of the other roller 208a, 208b (e.g., as in the first preferred embodiment described above).

In this embodiment, the movement of each roller 208a, 208b along its roller path 212a,212b (and the securing of each roller 208a,208b at a desired position along the roller path 212a,212b) is effected by rotation of a knob 240 at the end of a roller adjustment shaft 242. The roller adjustment shaft 242 has a threaded portion 244, and the support block 234 has a bore 246 that is correspondingly threaded, so that rotation of the roller adjustment shaft 242 (about a longitudinal axis of the roller adjustment shaft) moves the support block 234 along the threaded portion 244. For example, clockwise rotation of the roller adjustment shaft 242 (about its longitudinal axis) moves the support block 234 forward along the threaded portion 244 (i.e., away from the knob 240), and counterclockwise rotation of the roller adjustment shaft 242 (about its longitudinal axis) moves the support block 234 backward along the threaded portion 244 (i.e., toward the knob 240). The cooperating threads prevent movement of the support block 234 unless the roller adjustment shaft 242 is rotated (this secures the support block 234 at the desired location once the knob 240 is released).

While there has been described and illustrated specific embodiments of the invention, it will be apparent to those skilled in the art that variations and modifications are possible without deviating from the broad spirit and principle of the invention. The invention, therefore, shall not be limited to the specific embodiments discussed herein.

What is claimed is:

1. A rod bender for bending a surgical rod for use in spine surgery, comprising:
a ram shaft having a distal end having an arcuate rod contact surface, the ram shaft extending parallel to a plane and being moveable, along a shaft path that is parallel to the plane, through a plurality of positions including a ram shaft proximal position and a ram shaft distal position, the ram shaft distal position being a position in which the arcuate rod contact surface is in a distal contact surface position; and
a pair of cylindrical rollers, each having a curved roller surface, the rollers being disposed relative to the plane such that the shaft path passes between the rollers, each roller being rotatably mounted relative to the plane such that a rotation axis of each roller is perpendicular to the plane, each roller being moveable relative to the distal contact surface position, along a respective roller path that is parallel to the plane, through a plurality of positions including a roller proximal position and a roller distal position;
wherein a straight rod, disposed perpendicular to the shaft path when the ram shaft is in the ram shaft proximal position, is bendable by movement of the ram shaft toward the ram shaft distal position as the arcuate rod contact surface pushes the rod while the curved roller surfaces resist movement of the rod; and
wherein each roller is rotatably mounted at a distal end of a respective roller shaft, each roller shaft extending parallel to the plane, such that the rotation axis of each roller is perpendicular to a longitudinal axis of its respective roller shaft, wherein each roller shaft has a proximal end, and the proximal ends of the roller shafts are hinged to one another about a roller shaft hinge axis, the roller shaft hinge axis being perpendicular to the plane, at a roller shaft hinge point between the rollers and forward of the shaft path, whereby rotation of each roller shaft about the roller shaft hinge axis moves its associated roller along the roller path of the associated roller.

2. The rod bender of claim 1, further comprising a roller adjustment shaft extending parallel to the plane, the roller adjustment shaft being rotatable about a longitudinal axis of the roller adjustment shaft, the roller adjustment shaft being coupled to at least one of the rollers such that rotation of the roller adjustment shaft in one direction moves the at least one of the rollers toward its respective roller proximal position, and such that rotation of the roller adjustment shaft in an opposite direction moves the at least one of the rollers toward its roller distal position.

3. The rod bender of claim 2, wherein at least one of the roller shafts is coupled to a threaded bore within which to roller adjustment shaft threads, such that rotation of the roller adjustment shaft about the longitudinal axis of the roller adjustment shaft threads the roller adjustment shaft within the threaded bore to move the roller shaft along the roller adjustment shaft.

4. The rod bender of claim 1, further comprising a pair of roller adjustments shafts extending parallel to the plane, each roller adjustment shaft being rotatable about a longitudinal axis of the roller adjustment shaft, each roller adjustment shaft being coupled to a respective one of the roller shafts such that rotation of the roller adjustment shaft in one direction rotates the respective one of the roller shafts about the roller shaft hinge axis to move its associated roller toward the roller proximal position of the associated roller, and such that rotation of the roller adjustment shaft in an opposite direction rotates the respective one of the roller shafts about the roller shaft hinge axis to move its associated roller toward the roller distal position of the associated roller.

5. The rod bender of claim 4, wherein each roller adjustment shaft is coupled to its associated roller shaft by a coupling pin, the coupling pin seating into a bore through a central portion of the associated roller shaft, the coupling pin having a threaded bore within which the roller adjustment shaft threads, such that rotation of the roller adjustment shaft about the longitudinal axis of the roller adjustment shaft threads the roller adjustment shaft within the threaded bore to move the coupling pin along the roller adjustment shaft and thereby push the coupling pin against the bore of the associated roller shaft to rotate the associated roller shaft about the roller shaft hinge axis.

6. The rod bender of claim 1, further comprising a lever having a distal end that is rotatably mounted relative to the plane about a lever hinge axis that is parallel to the plane and that is perpendicular to the shaft path, the lever being mechanically connected to the ram shaft, wherein rotation of the lever toward a lever proximal position pulls the ram shaft toward the ram shaft proximal position, and wherein rotation of the lever toward a lever distal position pushes the ram shaft toward the ram shaft distal position.

7. The rod bender of claim 6, wherein the lever further has a central portion, and the rod bender further comprises a cam having a proximal end and a distal end, the proximal end of the cam being rotatably mounted to the central portion of the lever about a proximal cam hinge axis parallel to the lever hinge axis, the distal end of the cam being rotatably mounted to the proximal end of the ram shaft about a distal cam hinge axis parallel to the lever hinge axis, wherein rotation of the lever toward the lever proximal position pulls the cam and thereby pulls the ram shaft toward the ram shaft proximal position, and wherein rotation of the lever toward the lever distal position pushes the cam and thereby pushes the ram shaft toward the ram shaft distal position.

8. A rod bender for bending a rod, comprising:
   a ramming surface providing element disposed parallel to a plane, the ramming surface providing element being movable along a ramming path that is parallel to the plane, the ramming surface providing element having a ramming surface that contacts and pushes a rod as the ramming surface providing element is moved along the ramming path;
   a plurality of resistance surface providing elements, each being positionable at a variety of positions adjacent the ramming path such that the ramming path passes between at least two of the resistance surface providing elements, each of the resistance surface providing elements having a resistance surface against which the rod is pushed by the ramming surface as the ramming surface providing element is moved along the ramming path;
   wherein the rod is bendable by the ramming surface providing element pushing the rod, with the ramming surface, between the at least two of the resistance surface providing elements while the resistance surfaces resist movement of the rod; and
   wherein the rod is bendable into any one of a plurality of arc shapes, and wherein each possible positioning of the resistance surface providing elements determines a respective one of the plurality of arc shapes; and
   wherein each resistance surface providing element is mounted at a distal end of a respective support shaft, each support shaft extending parallel to the plane, wherein each support shaft has a proximal end, and wherein the proximal ends of the support shafts are hinged to one another about a support shaft hinge axis, the support shaft hinge axis being perpendicular to the plane, at a support shaft hinge point between the resistance surface providing elements and forward of the ramming path, whereby rotation of either support shaft about the support shaft hinge axis moves its associated resistance surface providing element.

9. The rod bender of claim 8, wherein each resistance surface providing element is mechanically coupled to a respective adjustment shaft extending parallel to the plane, each adjustment shaft being rotatable about a longitudinal axis of the adjustment shaft, such that rotation of the adjustment shaft moves its associated resistance surface providing element.

10. The rod bender of claim 9, wherein each adjustment shaft is coupled to its associated resistance surface providing element by a coupling element, the coupling element having a threaded bore within which the adjustment shaft threads, such that rotation of the adjustment shaft about the longitudinal axis of the adjustment shaft threads the adjustment shaft within the threaded bore to move coupling element along the adjustment shaft and thereby move its associated resistance surface providing element.

11. The rod bender of claim 8, is wherein each adjustment shaft is coupled to a respective one of the support shaft by its associated coupling element the coupling element seating into a bore through a central portion of the associated support shaft, such that rotation of the adjustment shaft about the longitudinal axis of the adjustment shaft threads the adjustment shaft within the threaded bore to move the coupling element along the adjustment shaft and thereby push the coupling element against the bore of the associated support shaft to rotate the associated support shaft about the support shaft hinge axis.

12. The rod bender of claim 8, further comprising a leverage providing element mechanically connected to the ramming surface providing element, the leverage providing element providing leverage for moving the ramming surface providing element with a force sufficient to bend the rod.

13. The rod bender of claim 12, wherein the leverage providing element has a distal end that is rotatably mounted relative to the plane about a hinge axis that is parallel to the plane and that is perpendicular to the ramming path, wherein rotation of the leverage providing element about the hinge axis moves the ramming surface providing element.

14. The rod bender of claim 13, wherein the leverage providing element further has a central portion, and the rod bender further comprises a cam element having a proximal end and a distal end, the proximal end of the cam element being rotatably mounted to the central portion of the leverage providing element about a proximal cam axis parallel to the hinge axis, the distal end of the cam element being rotatably mounted to the proximal end of the ramming surface providing element about a distal cam axis parallel to the hinge axis, wherein rotation of the leverage providing element moves cam element that moves the ramming surface providing element.

* * * * *